(12) United States Patent
Aghassi et al.

(10) Patent No.: US 6,489,171 B1
(45) Date of Patent: Dec. 3, 2002

(54) CHEMICAL DISPENSING SYSTEM AND METHOD

(75) Inventors: Nora B. Aghassi, Austin, TX (US); Kim G. Franceschini, Austin, TX (US); Paul J. Ardi, Austin, TX (US)

(73) Assignee: Cell Marque Corporation, Hot Springs, AR (US)

( * ) Notice: Subject to any disclaimer, the term of this patent is extended or adjusted under 35 U.S.C. 154(b) by 0 days.

(21) Appl. No.: 08/844,553

(22) Filed: Apr. 18, 1997

(51) Int. Cl.[7] .................................................. B01L 3/00
(52) U.S. Cl. ..................... 436/180; 422/61; 422/100; 422/102; 427/2.11; 427/2.13; 435/287.3; 435/288.3; 435/305.1; 436/46
(58) Field of Search ........................... 422/100, 99, 102, 422/61; 436/46, 180, 174; 427/2.11, 2.13; 359/396, 397, 398; 435/287.3, 288.3, 305.1

(56) References Cited

U.S. PATENT DOCUMENTS

| | | | |
|---|---|---|---|
| 4,358,470 A | * | 11/1982 | Rasmussen |
| 4,731,335 A | * | 3/1988 | Brigati .......................... 436/180 |
| 5,225,325 A | | 7/1993 | Miller et al. |
| 5,232,664 A | | 8/1993 | Krawzak et al. |
| 5,322,771 A | | 6/1994 | Rybski et al. |
| 5,418,138 A | | 5/1995 | Miller et al. |
| 5,595,707 A | | 1/1997 | Copeland et al. |
| 5,686,313 A | * | 11/1997 | Sitte et al. |
| 5,804,141 A | * | 9/1998 | Chianese ........................ 422/63 |

OTHER PUBLICATIONS

Brochure entitled, "When Everything Counts . . . The OptiMax Plus Automated Cell Staining System is the Obvious Choice," by BioGenex, pp. 1–6.
Brochure entitled, "NEXES IHC Staining System," pp. 1–2.
BioTek Solutions Inc. TechMate 1000 Operator's Manual, 355 pages.

* cited by examiner

*Primary Examiner*—Jan Ludlow
(74) *Attorney, Agent, or Firm*—Jackson Walker LLP

(57) ABSTRACT

A system and method for applying one or more chemicals to a tissue sample is provided. The system preferably includes a cassette for housing a slide device, a film, and an injection system. The slide device preferably includes a specimen slide for containing the tissue sample and a cover plate connected to the specimen slide. The film is preferably moveable through the cassette along guide rollers and preferably contains a plurality of containers containing one or more chemicals. The injection system may include a piston for displacing the chemicals from the containers through an injection port to the tissue sample. The cassette may be placed on a cassette driver that contains a motor-driven shaft for driving the piston and moving the film.

9 Claims, 15 Drawing Sheets

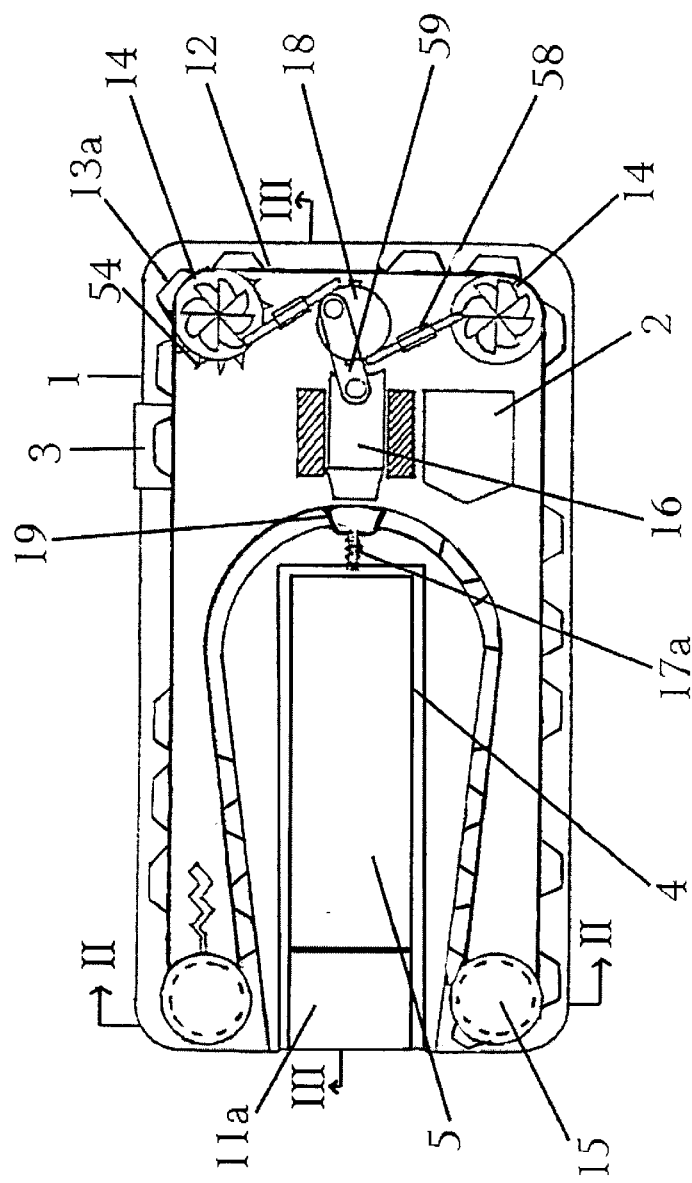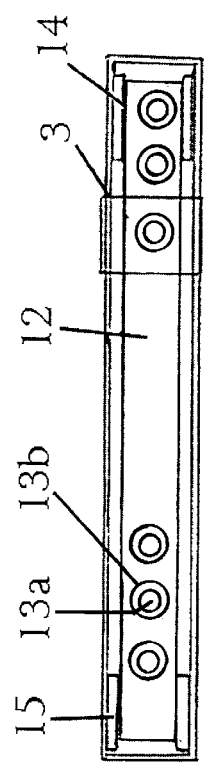
FIG. 3A
FIG. 3B

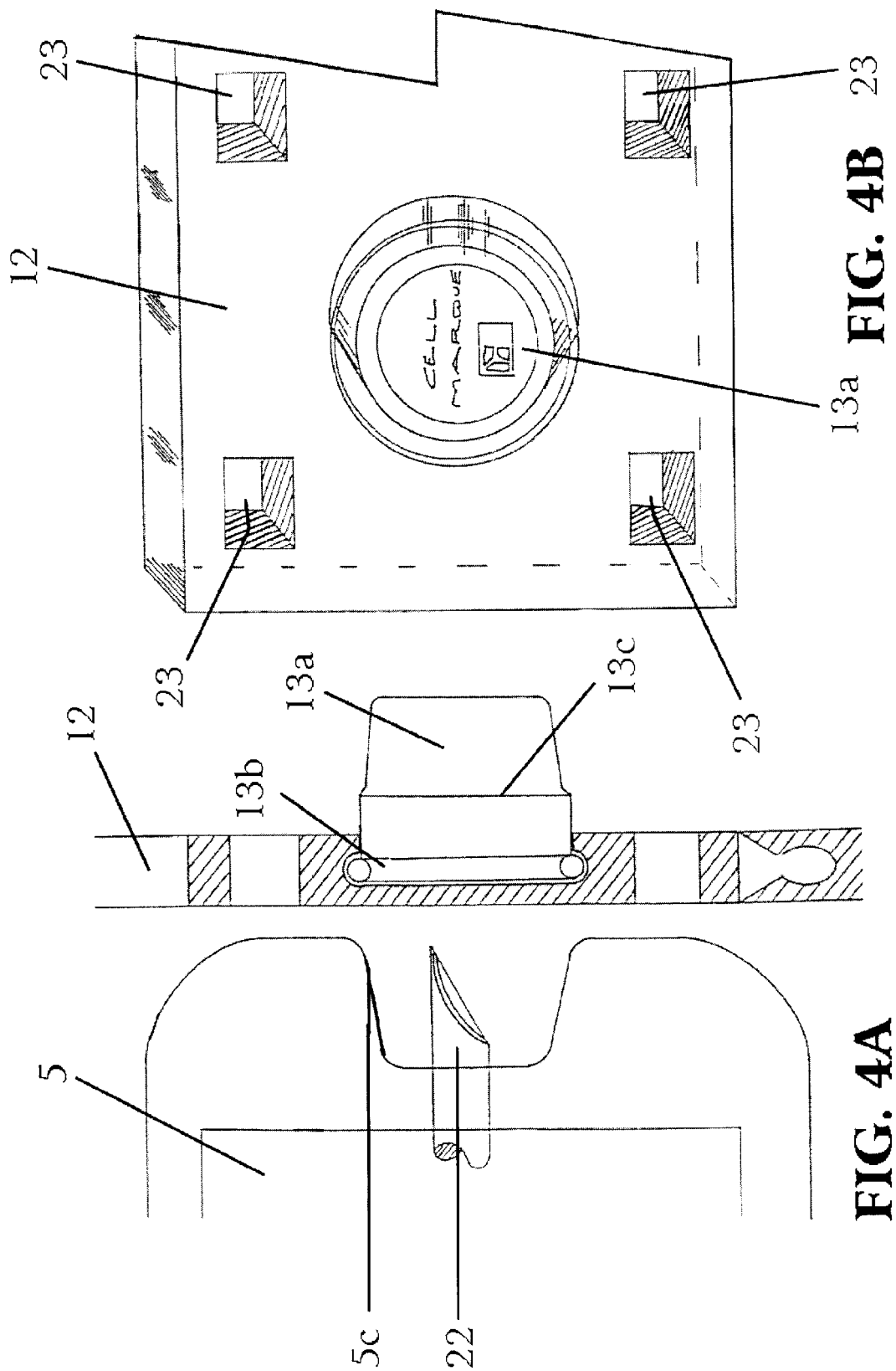

CHEMICAL DISPENSING SYSTEM AND METHOD

BACKGROUND OF THE INVENTION

1. Field of the Invention

This present invention relates to histological and molecular pathology and more specifically to an immunohistochemistry staining system for staining tissue samples with a variety of chemicals to facilitate examination of the samples.

2. Description of the Related Art

Staining tissue with chemicals is generally well known in the field of molecular pathology. Tissue samples may be subjected to histological and molecular pathological tests including in-situ hybridization, polymerase, and to chemical stains which are commonly referred to as "special stains". A variety of chemicals may be used in the staining process, including biological reagents, antibodies, buffers, and deionized water. After a tissue is stained and rinsed with certain chemicals, one skilled in the art can identify the tissue type and any abnormalities in the tissue. Such methods may be used to identify various diseases in the tissue. Several methods of staining tissue are currently in use.

One conventional method utilizes capillary action in which a chemical in liquid state is drawn up a narrow space between two slides due to the attraction between the molecules of the chemical and the slides. One of the slides contains a tissue sample to be contacted with the chemical. An operator is generally required to pipette the appropriate staining chemicals into containers into which the slides are placed. Filling the containers tends to require a substantial amount of time. The slide pair is then manually or mechanically inserted vertically into each container in an order dependent on the type of chemical in each container. Manually placing the slide pair in the correct container may be difficult if the containers are not labeled for the appropriate chemical. The method may be also be difficult when performed mechanically if a mechanical arm is not properly programmed to move the slide pair sequentially to the proper containers. A computer may be used to program the movements of a mechanical arm. The of time that the slide pair is in each container is determined by using a watch or a computer.

Another method for staining tissue uses an automated dispensing head or nozzle to drop or spray chemicals onto a slide's upper surface which contains the tissue sample. This may also be performed manually. An evaporation inhibitor is placed over the slide after a chemical agent is placed onto the tissue sample. The movable dispensing head draws the desired chemical from a container and dispenses the chemical on top of the appropriate slide. One limitation of this method is that a drop of liquid may form at the tip of the head after each dispensing operation and may drop onto another slide as the head moves. Also, the containers need to be filled with chemicals before they are dispensed, which requires labor. The length of time that elapses before each chemical is washed from a slide may be controlled by a computer.

A similar method involves dispensing a chemical from a dispenser pre-packaged with the chemical so that a person does not have to fill the dispenser. After each dispensing operation, the dispenser withdraws the drop remaining on the tip of its nozzle to prevent the drop from falling on a slide. The dispenser is placed in a rotating tray located above a slide tray. The tray moves the dispenser above the slide on which a chemical is dispensed. A computer is used to control the movement of the tray and to determine the length of time before a chemical is washed from a slide.

U.S. Pat. No. 5,232,664 relates to a dispenser for delivering small amounts of liquid to a sample. The dispenser includes a reservoir chamber linked to a dispense chamber. The dispense chamber communicates with a nozzle through an outlet line. A number of such dispensers are positionable within a reagent tray that is rotated by a drive carousel to perform an immunoassay. This patent and U.S. Pat. No. 5,595,707 are incorporated by reference as if fully set forth herein.

Turning to another method, chemicals may also be dispensed manually or from a mechanical transfer head into a gap between a cover plate and a slide containing a tissue sample. The slide and cover plate are in vertical positions. Gravity forces the chemicals through the gap. The surface tension between the slides prevents chemicals from flowing immediately out of the bottom of the gap. The transfer head may be filled with the appropriate chemical after each dispensing. Such a method requires significant time and labor. A computer may be used to control the movements of the transfer head and to time how long a slide is exposed to each chemical.

The methods presented above tend to be problematic. Some of the methods involve steps that are manually performed and require a significant amount of time. For example, an operator may be required to pipette a chemical onto a slide and/or fill chemical containers used for staining tissue. The operator may also have to carefully label these containers and time how long each chemical contacts the tissue. Such processes are labor-intensive and may be subject to significant variation due to human error. Further, some of the methods require the use of expensive automated equipment and a computer to control the equipment.

It is therefore desirable that an improved tissue staining system be derived which is less labor intensive. Further, it is desirable that the system requires less expensive equipment to stain the tissue. A system with these features would tend to increase the quality of the resulting stained tissue while reducing operating costs.

SUMMARY OF THE INVENTION

The problems outlined above are in large part solved by an improved tissue staining system and method of the present invention. That is, the system hereof does not require expensive equipment such as a computer in order to function. Further, the system may be automated such that less labor is needed to operate the system.

An embodiment of the system includes a cassette for housing the staining system. The cassette preferably has an open end into which a removable slide device may be placed. The slide device preferably includes a specimen slide for holding a tissue sample and a cover plate located above the specimen slide. A film is preferably located within the cassette for delivering one or more chemicals to the slide device. As described herein, a "chemical" is taken to mean any substance added to the tissue sample to facilitate testing or examination of the tissue sample, including but not limited to a biological reagent, an antibody, a buffer, a label, a chromogen, a solvent, a resin and/or deionized water. Each chemical may be reactive or unreactive with the tissue sample.

The specimen slide and cover plate are preferably attached together in spaced relation to form a head space therebetween. A plastic (e.g., mylar) spacer may be placed between the cover plate and specimen slide. This spacer preferably creates the head space and preferably seals the outer edges of the slide device. The slide device may be held together with a slide holder. Alternately, the specimen slide and the cover plate may be constructed such that they can be snapped together to form a fixable engagement. On opposite ends of the slide device, an injection port and a relief port preferably communicate with the head space formed within the slide device. The injection port preferably includes a conduit, and that conduit preferably has a pointed end. A chemical may be passed through the injection port into the head space and then out of the head space through the relief port.

The slide device may be placed into the open end of the cassette. An injection piston preferably located within the cassette adjacent to the injection port may reciprocate in a direction toward the injection port. This reciprocating motion preferably enables the injection piston to contact containers disposed on the film. The containers contain one or more chemicals to be applied to the tissue sample, and holders may be used to attach the containers to the film. The film preferably extends along the edge of the cassette and forms a loop (e.g., in a horseshoe shape) in the interior of the cassette. Guide rollers within the cassette preferably move the film through the cassette such that the containers disposed within the film are passed to a location between the injection piston and the injection port.

The reciprocating motion of the injection piston is preferably synchronized with the movement of the film such that the piston contacts each holder of the film. In the case that a container is disposed within the holder contacted by the piston, the piston preferably forces the container against the pointed conduit end within the injection port. The pointed conduit end preferably punctures the container. The container preferably ruptures, causing the chemical(s) within the container to be released into the injection port. The piston preferably creates pressure within the injection port to cause the released chemical(s) to be positively displaced through the injection port and into the head space to stain the tissue sample. In the case that the head space contains a chemical that has been previously injected, such previously injected chemical is preferably displaced out of the head space by the pressure derived from the piston. The displaced waste chemical is preferably passed through the relief port and into a waste tank. The waste tank preferably contains absorbent material to facilitate collection of such waste chemicals.

The holders of the containers are preferably spaced apart by equal distances along the length of the film. The contact time between a chemical and a tissue sample is preferably determined by the distance between containers on the film. A specified number of holders may be left empty to create a predetermined amount of time between (a) the injection of a first chemical into the head space and (b) the injection of a second chemical into the head space and the simultaneous displacement of the first chemical from the head space. The motion of the film and the displacement of the injection piston are preferably synchronized such that each holder in the film is contacted by the injection piston.

The containers may hold more than one chemical. In an embodiment, two or more chemicals within the containers are separated by an interior wall within the container to prevent the chemicals from mixing before injection. When a container holding more than one chemical is forced against the pointed conduit end, each of the wall segments within the container is preferably punctured to allow the chemicals to mix before being injected into the slide device.

In an embodiment, the cassette may be placed onto a cassette driver for driving the guide rollers and the injection piston. The cassette driver preferably includes a shaft which may extend from the top of the cassette driver into the bottom of the cassette. The shaft is preferably a spline joint shaft which may be connected to the guide rollers and the piston. A gear drive motor preferably rotates the shaft at a constant speed, causing the guide rollers and the piston to move at a constant speed.

The cassette driver also preferably includes a heat pad and a thermostat for controlling the temperature of the chemicals in the head space of the slide device. The heat pad may be used to heat or cool the tissue sample and chemicals in the head space. The thermostat may maintain the heat pad within a predetermined temperature range or it may cause pulse changes in the temperature of the heat pad. In this way, the tissue and chemicals may be subjected to any pre-defined temperature profile. Maintaining the temperature of the tissue sample and chemicals within a selected range may facilitate or control reaction of the injected chemicals with the tissue sample. The cassette may be engaged with the cassette driver such that the heat pad is positioned under the slide device. The cassette driver preferably contains a pressure sensitive switch enabling automatic activation of the cassette driver motor when the cassette is detected on top of the cassette driver. A pre-set timing device may be used to stop the motor after a predetermined amount of chemicals have contacted the tissue sample.

In an embodiment, the tissue staining system includes a plurality of cassette drivers and a control panel for individually operating each of the cassette drivers. The control panel is preferably coupled to the motor and heat pad of each of the cassette drivers. A plurality of cassettes may be placed on the cassette drivers to allow a plurality of tissue samples to be stained simultaneously.

In an alternate embodiment, a portable cassette includes a battery operated solenoid piston for injecting chemicals into a slide device. The slide device is preferably located proximate the center of the cassette. The portable cassette preferably includes a twin drive motor for rotating guide rollers to move a film. The film preferably delivers containers to the solenoid piston. The portable cassette preferably includes a heat pad located under the slide device and a waste tank for collecting chemicals which are displaced from the slide device. The portable cassette may include printed contacts for activating the heat pad and/or the solenoid piston.

Each of the embodiments discussed above may be combined or used individually.

Further advantages of the present invention will become apparent to those skilled in the art with the benefit of the following detailed description of the preferred embodiments and upon reference to the accompanying drawings.

BRIEF DESCRIPTION OF THE DRAWINGS

FIG. 3a is a top plan view of an interior portion of the cassette.

FIG. 3b is a side view of the interior portion of the cassette.

FIG. 3c is a cross-sectional view along plane II of FIG. 3a.

FIG. 3d is a cross-sectional view along plane III of FIG. 3a.

FIG. 4a is a top plan view of an injection end of the slide device and a portion of a film.

FIG. 4b is a front view of a portion of the film.

Figure 1A:
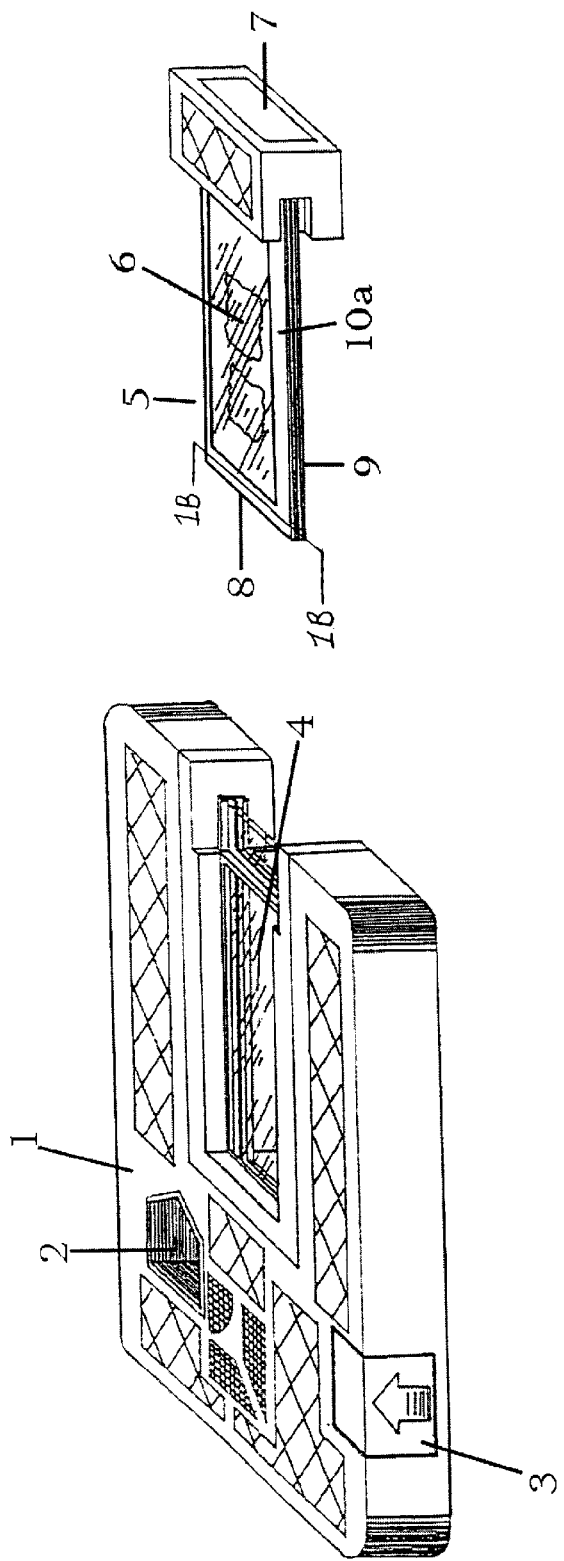
FIG. 1a is a perspective view of a cassette, a slide device, and a slide holder which are part of a tissue staining system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DESCRIPTION OF THE PREFERRED EMBODIMENTS

Turning now to one embodiment of the present invention, FIG. 1 illustrates an outside perspective view of cassette 1 which is part of an improved tissue staining system. As described herein, "cassette" is taken to include any housing for containing a tissue sample to facilitate the application of chemicals onto the tissue sample. The cassette in FIG. 1 is substantially rectangular and contains an optional protective covering on its top surface that covers the interior portion of the cassette. It is to be appreciated that the cassette could have any of a variety of shapes (e.g., circular, triangular, etc.). Cassette 1 preferably contains a film access door 2 that may be located on the top, bottom, or side of the cassette. Cassette 1 preferably further includes a container access door 3 to allow access to an interior portion of the cassette.

FIG. 1a illustrates slide device 5 into which a tissue sample 6 may be placed. Slide device 5 preferably includes a specimen slide 9 and a cover plate 8. A spacer 10a is preferably placed between specimen slide 9 and cover plate 8. The spacer may be made of a plastic such as mylar. Spacer 10a preferably extends along the length of slide device 5 and seals the outer edges of the slide device to maintain chemical between the specimen slide and the cover plate. A slide holder 7 preferably holds slide device 5 together by clamping specimen slide 9 to cover plate 8 at one end of slide device 5. An open end 4 of cassette 1 is preferably shaped to receive slide device 5.

Figure 1B:
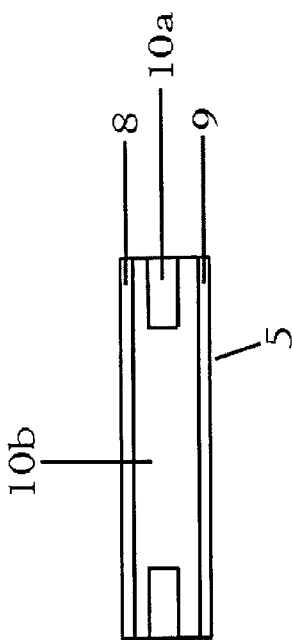
FIG. 1b depicts a cross-section of the slide device.

FIG. 1b depicts a cross-section of slide device 5 taken along plane I. Cover plate 8 is preferably located above specimen slide 9. Spacer 10a is preferably located between cover plate 8 and specimen slide 9 at their outer edges. The thickness of spacer 10a is preferably in the range between about 0.0005 inch and about 0.004 inch, more preferably between about 0.001 inch and about 0.002 inch, and even more preferably about 0.0015 inch. The thickness of spacer 10a preferably creates a head space 10b between cover plate 8 and specimen slide 9. The head space between cover plate 8 and specimen slide 9 preferably has a width that is the same as the thickness of spacer 10a. When chemicals are injected into slide device 5, they preferably fill head space 10b and interact with tissue sample 6. Spacer 10a may be disposed about the entire perimeter of the slide device to surround the head space.

Figure 1C:
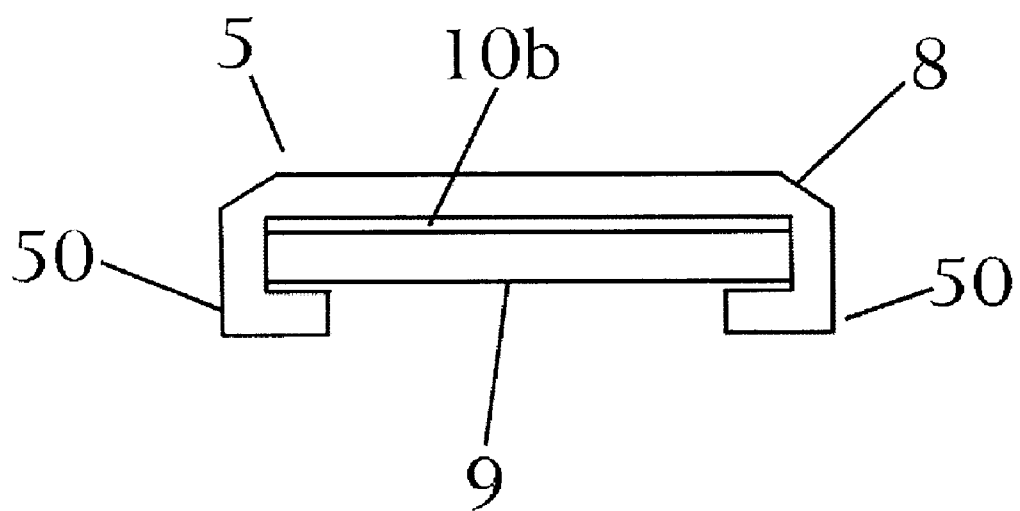
FIG. 1c depicts a side view of an alternate embodiment of the slide device.

In an alternate embodiment, specimen slide 9 and cover plate 8 are capable of being attached in fixable engagement without slide holder 7. The specimen slide and cover plate may be snapped together. Alternately, the cover plate may contain substantially L-shaped members 50 as depicted in FIG. 1c, which depicts a cross sectional view of slide device 5. The L-shaped members serve as a base for supporting specimen slide 9, which may be slid into engagement with cover plate 8. The tolerance between the specimen slide and the cover plate is preferably sufficiently low to prevent liquid chemical from exiting head space 10 through the outer edges of the slide device.

Figure 2:
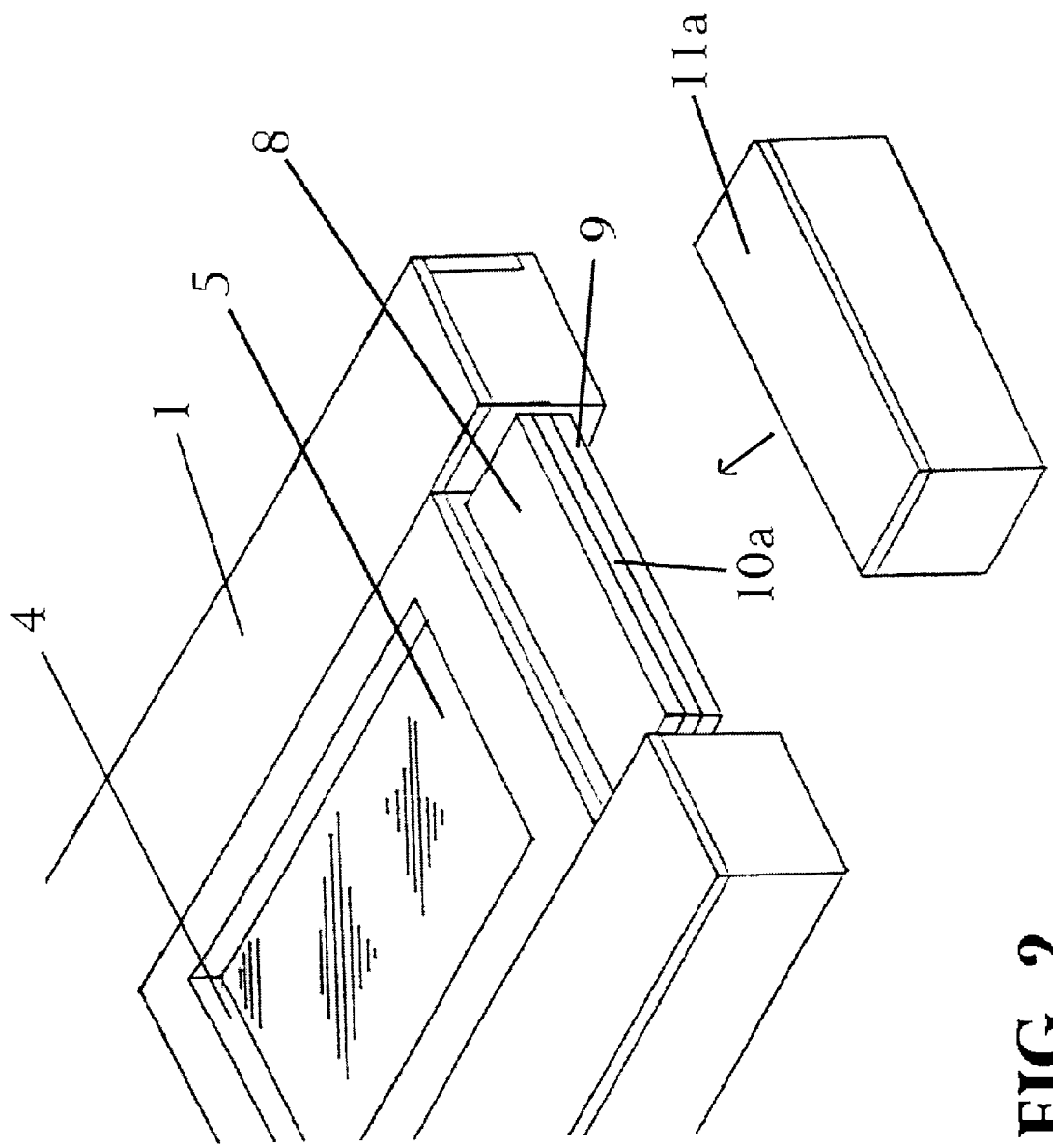
FIG. 2 is a perspective view of the cassette depicting the slide device engaged within the cassette.

FIG. 2 illustrates slide device 5 positioned within open end 4. A waste tank 11a is preferably placed in open end 4 near the end of slide device 5. The waste tank may be used to collect waste chemical that exits head space 10b. The waste tank is preferably detachable from the end of slide device 5 to allow it to be removed and replaced. In an embodiment, the waste tank contains absorbent material to facilitate removal of the waste chemical. Preferably, this absorbent material is an absorbent non-woven structure.

FIG. 3a depicts a top plan view of an interior portion of cassette 1. Slide device 5 and waste tank 11 are preferably located in open end 4 of cassette 1 during the tissue staining process. A film 12 is preferably used to deliver chemicals to slide device 5 for application onto the tissue sample. The film is preferably substantially flexible and may be a polymeric film, a ribbon film, or any belt-like member that is sufficiently flexible to be drawn around guide rollers 14 and 15 and moved through cassette 1. Film 12 may be loaded into and removed from the cassette through film access door 2. Film 12 preferably extends about the perimeter of cassette 1 and may form a horseshoe-shaped loop within the interior portion of the cassette.

Guide rollers 14 and 15 may contain sprockets and preferably engage film 12. The guide rollers are preferably connected to shaft 18 via secondary shafts 58. Shaft 18 is preferably a splined shaft that is rotatable to cause guide rollers 14 to rotate. Rotation of the guide rollers preferably causes movement of the film throughout the cassette. A plurality of containers 13a are preferably disposed on the film. Each container 13a preferably contains between about 50 microliters and about 200 microliters of chemical, and more preferably between about 100 microliters and about 150 microliters of chemical.

Guide rollers 15 preferably engage film 12 and rotate to move the film about the cassette and through the horseshoe-shaped loop depicted in FIG. 3a. The cassette preferably includes an injection system for injecting chemicals into injection port 17. The injection system preferably includes an injection piston 16 located near an end of slide device 5. Piston 16 is preferably attached to rotating shaft 18 via cam 59 which displaces the piston in a direction toward the film 12 at a location proximate the apex of the horseshoe-shaped loop. Piston 16 preferably reciprocates along an imaginary axis that extends longitudinally through injection port 17. Piston 16 preferably contacts container 19 and ruptures the container to release chemical into injection port 17. Injection port 17 and relief port 21 preferably communicate with the head space and may be disposed on opposite ends of the slide device. The piston preferably creates pressure is within injection port 17 to force the chemical through the injection port and into the head space 10b where it contacts the tissue sample.

FIG. 4a depicts a top plan view of conduit 22 which preferably forms a portion of injection port 17 of slide device 5. Conduit 22 preferably includes a sharp or pointed end for puncturing containers as depicted in FIG. 4a. The piston preferably contacts the containers and forces them against hollow conduit 22. The containers preferably rupture as a result of the contact with conduit 22 and piston 16 and the chemical within the ruptured container is preferably directed through conduit 22 into the head space under pressure derived from the reciprocating motion of the piston. Film 12 preferably carries container 13a to a location adjacent to the sharp end of conduit 22. The film is preferably sufficiently flexible to bend to allow container 13a to be pressed against the end of conduit 22.

In an embodiment, container 13a contains two or more chemicals to be injected into slide device 5. In some cases it may be necessary to simultaneously apply two or more chemicals to the tissue sample without mixing the chemicals beforehand. Container 13a may contain an interior wall having one or more wall segments 13c for compartmentalizing the container to prevent the mixing of two or more chemicals within the container prior to injection. Wall 13c is preferably punctured by conduit 22 during injection to allow the chemicals to mix as they are injected into slide device 5. The chemicals are preferably positively displaced from container 13a into head space 10b where they contact the tissue sample. In the case that a first chemical resides in head space 10b at the time a second chemical is injected into container 13a, the first chemical is preferably positively displaced through relief port 21 out of head space 10b by the second chemical and/or the pressure within the head space derived from piston 16.

FIG. 3b depicts a side view of cassette 1. Film 12 preferably includes a plurality of holders 13b for attaching containers 13a to the film. Holders 13b of film 12 are preferably spaced apart by equal distances. The containers 13a are preferably removable and replaceable on the film to allow the film to be reused after the tissue staining process has been completed. Container access door 3 preferably enables access to an interior portion of the cassette to allow containers to be placed into empty holders of the film after the film has been loaded into the cassette. In this manner, user-specified chemicals may be added to the film to be injected into slide device 5 to allow for customized staining protocols with respect to selection of the applied chemical.

The time of contact between a chemical and a tissue sample may be predetermined by the spacing between containers on the film. Selected holders may be left empty to increase the spacing between adjacent containers, thereby lengthening the contact time between a given chemical and the tissue sample. In operation, the reciprocation of the piston and the movement of the film preferably occur at constant speeds and are synchronized such that the piston contacts each holder on the film.

Figure 3D:
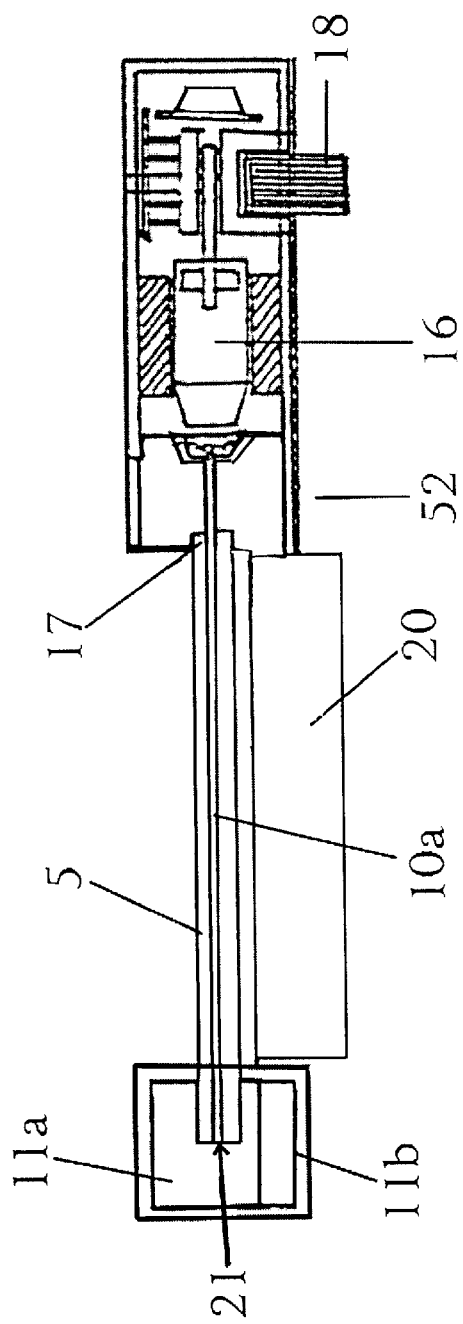
Figure 3C:
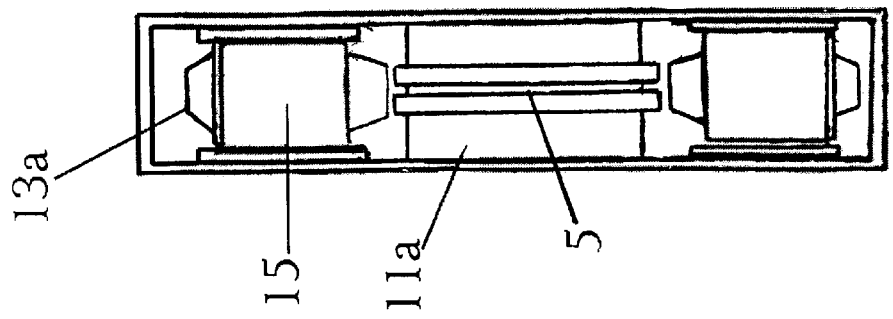

FIG. 3c further illustrates a cross-section of cassette 1 along plane II of FIG. 3a, depicting guide rollers 15 and an end of slide device 5. FIG. 3d is a cross-sectional view along plane III of FIG. 3a. A heat pad 20 is preferably located under slide device 5 to control the temperature of chemicals and tissue sample within head space 10b. Although heat pad 20 is shown in FIG. 3a to extend through an opening in base 52, it also may reside entirely within cassette 1 between base 52 and slide device 5. Heat pad 20 may be used to heat or cool the chemicals and tissue sample to control any reaction that may occur between the chemicals and the tissue sample. The temperature of the heat pad 20 is preferably controlled to maintain the temperature of the tissue sample and chemical within a predetermined range. The temperature of the heat pad may be continuously adjusted as a function of the type and/or amount of chemical(s) injected into the head space. Heat pad 20 may be any conventional heat exchange of thermoelectric device. Heating coils or conduits adapted to contain a heat transfer medium may be contained within heat pad 20 to control the temperature at its surface.

Waste tank 11a is preferably placed at the end of slide device 5 during the tissue staining process. An absorbent material 11b is preferably located in the bottom of waste tank 11a. The absorbent material 11b preferably absorbs waste chemical passing from relief port 21 and facilitates the disposal of the waste chemical.

FIG. 4b shows a side view of a portion of film 12 which preferably contains openings 23. Each of the guide rollers may contain teeth 54 (shown in FIG. 3a), which may be placed in openings 23 to attach film 12 to the guide rollers. The teeth preferably maintain the engagement between the film and the guide rollers as the film is moved through the cassette. Alternately, the guide rollers may be smooth and a frictional engagement between guide rollers 15 and film 12 is sufficient to allow the film to be moved when the guide rollers are rotated. The slide device may contain an indention 56 shaped to receive container 13a. Indention 56 preferably surrounds conduit 22 to allow container 13a to be forced within the indention during release of chemical from the container into conduit 22.

Figure 5:
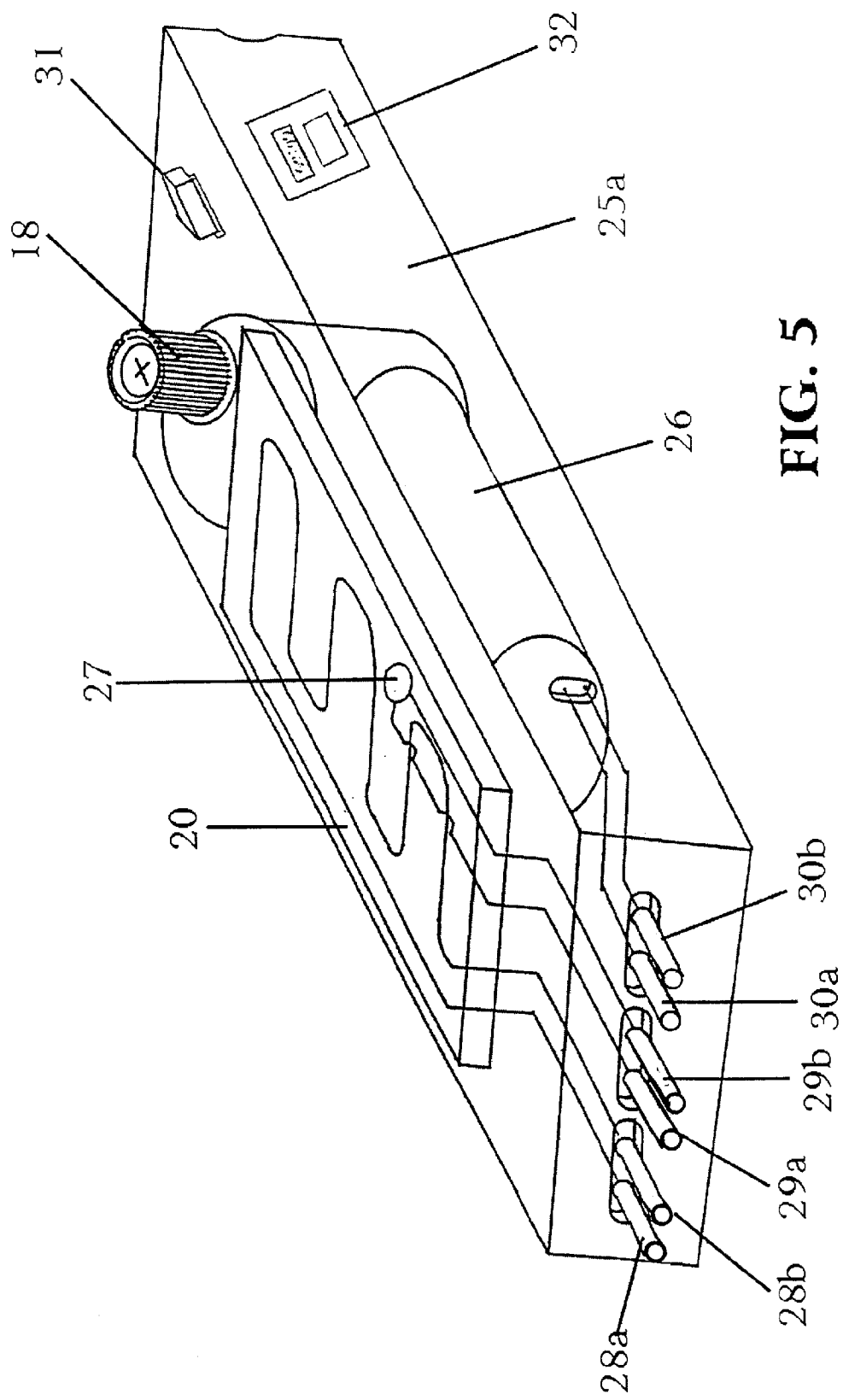
FIG. 5 is a perspective view of a cassette driver.

FIG. 5 depicts a cassette driver 25a for driving cassette 1. The bottom or base 52 of the cassette may be attached to the upper surface of the cassette driver. Shaft 18 preferably extends from the top of cassette driver 25a through an opening in base 52 of cassette 1. Shaft 18 is preferably a splined shaft. Shaft 18 is preferably rotated by a motor 26 at a constant speed. Motor 26 may be a gear drive motor. Shaft 18 preferably drives the motion of film 12 and piston 16 such that they are synchronized to allow each holder 13a in film 12 to be struck by piston 16.

Heat pad 20 is preferably located on the upper surface of cassette driver 25a. The cassette may contain an opening in base 52 sized to receive the heat pad such that the slide device engages the heat pad. The temperature of heat pad 20 is preferably controlled by thermostat 27. The heating contact leads 28a and 28b, the thermostat contact leads 29a and 29b, and the motor contact leads 30a and 30b are preferably located at one end of cassette driver 25a.

A pressure-sensitive switch 31 is preferably located on top of cassette driver 25a. When cassette 1 is placed on top of cassette driver 25a, switch 31 is preferably depressed to activate motor 26. A timing device 32 is preferably used to stop motor 26 after a predetermined amount of time that is sufficient to allow a selected amount of chemicals to be applied to the tissue sample.

Figure 6:
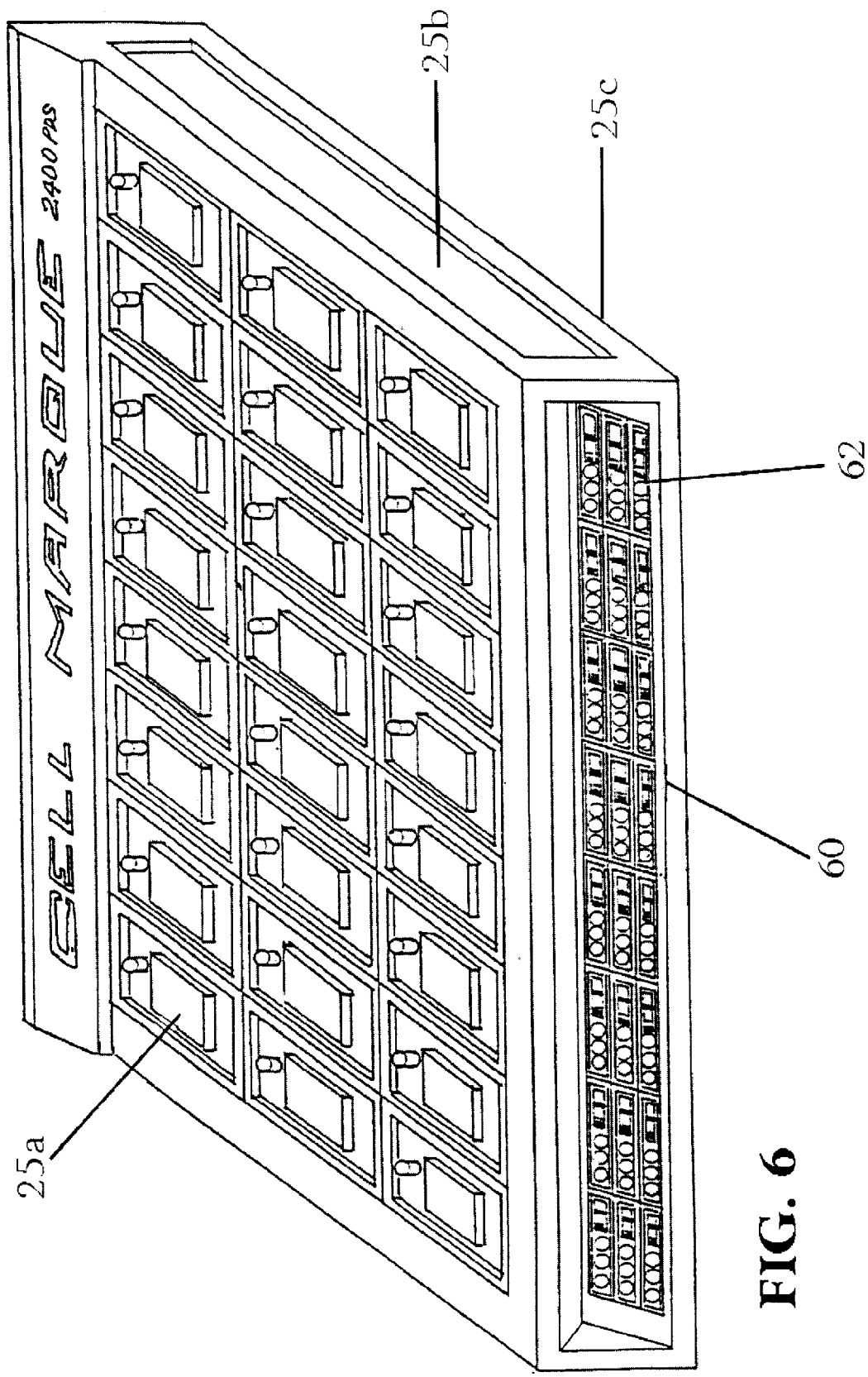
FIG. 6 is a perspective view of a multiple cassette driver unit.

FIG. 6 illustrates a multiple cassette driver unit 25b. Cassette drivers 25a are preferably located within a driver housing 25c. A cassette 1 may be placed on each cassette driver 25a to stain several tissue samples simultaneously.

The cassettes may be removed from the cassette driver and the slide device and film may be replaced before the cassette is reinserted on the cassette driver to stain a new tissue sample.

Multiple cassette driver unit preferably includes a control panel 60 for independently operating each of the cassette drivers. The control panel preferably includes a plurality of controllers 62 corresponding to each of the cassette drivers. Each controller is preferably electrically coupled to the motor 26 and heat pad 20. The controller may comprise a timer 32 for stopping motor 26 after a predetermined amount of running time. The controller may be further adapted to adjust the operating speed (rpm) of motor 26 to adjust the speed at which the film is moved and thus the rate that chemicals are applied to the tissue sample. The controller preferably includes manual switches to activate and stop motor 26. The controller may include a computer and a digital display indicating the temperature of the heat pad and the amount of time remaining on timer 32. The temperature of the heat pad may be adjusted manually using controller 62.

Figure 7:
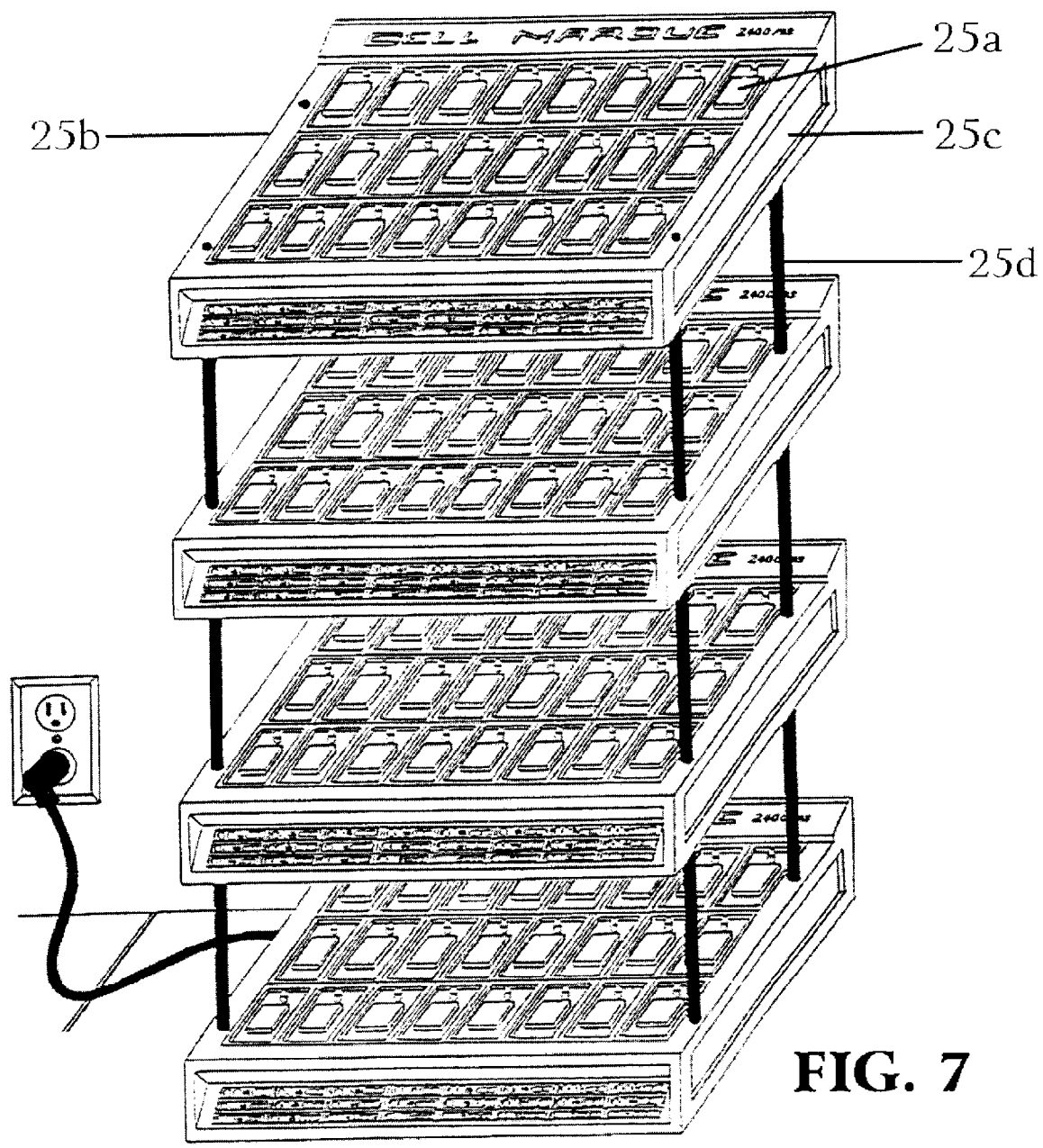
FIG. 7 is a perspective view of a multiple cassette driver system.

A system of multiple cassette driver units 25b is depicted in FIG. 7. A plurality of driver housings 25c preferably hold a plurality of cassette drivers 25a. Tray 25d preferably supports the multiple cassette driver units 25b, which are arranged vertically.

Figure 8:
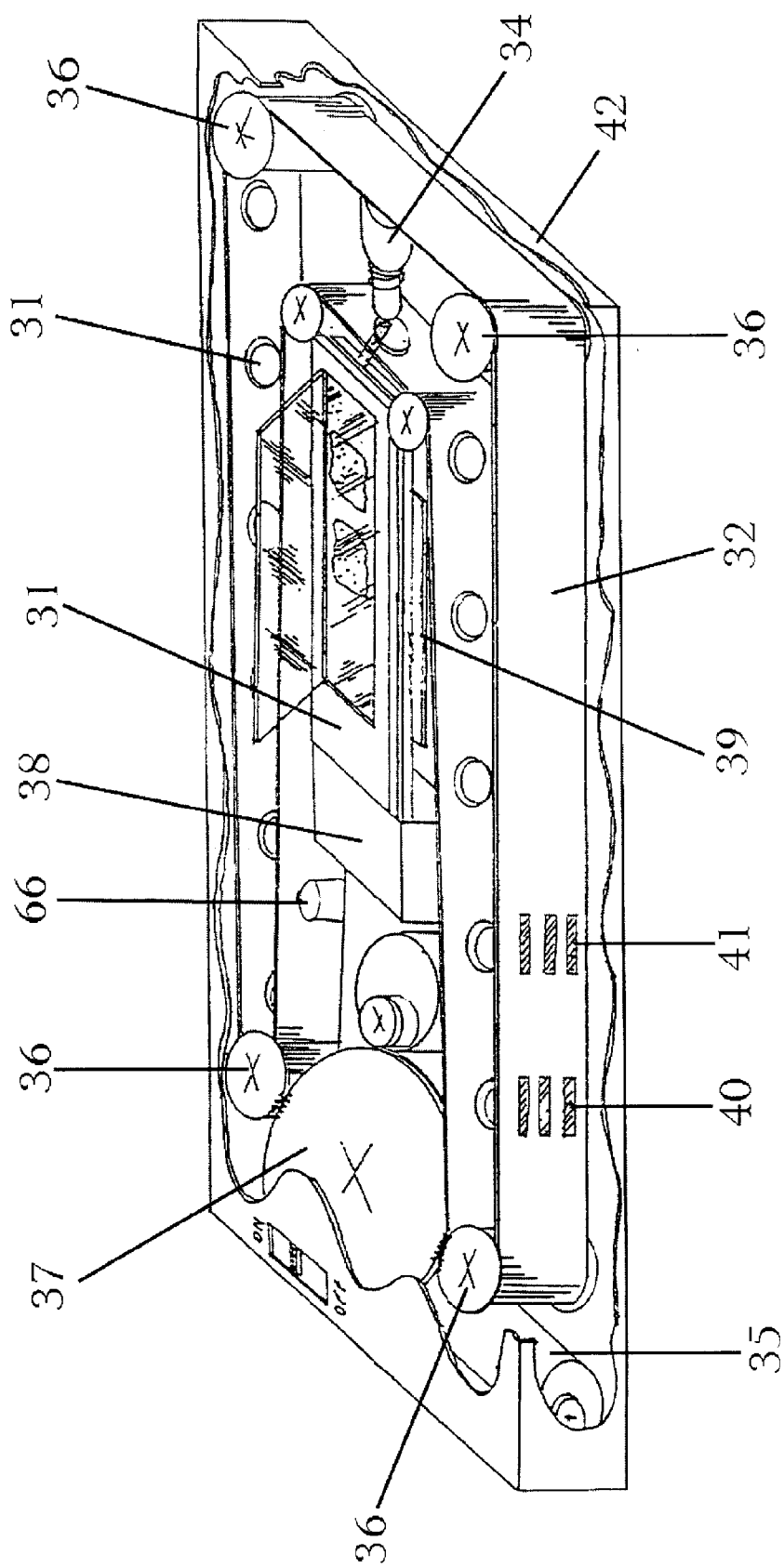
FIG. 8 is a perspective view of a portable cassette.

FIG. 8 depicts an alternate embodiment of the tissue staining system. The portable cassette 42 preferably includes a positive displacement slide device 31 into which the tissue sample may be placed. The portable cassette 42 preferably includes a film 32 which carries containers 33 to a solenoid piston 34. Solenoid piston 34 is operated by battery 35. The solenoid piston 34 preferably forces a chemical from each container 33 into slide device 31. Guide rollers 36 preferably rotate to move film 32, and the guide rollers 36 are preferably operated by a twin drive motor 37. A waste tank 38 is preferably located near the end of slide device 31 for collecting a chemical which exits slide device 31. A heat pad 39 is preferably located under slide device 31 which may control the temperature of chemicals within slide device 31. The presence or absence of contacts along the length of film 32 may produce closed or open circuits which in turn prevent or allow the passage of current. The current may activate the heat pad or actuate the solenoid. Contacts such as contacts 40 and contacts 41 may be placed in multiple rows along film 32 to allow multiple circuits to be opened or closed simultaneously or independently as the contacts pass by and come in contact with switches (e.g., switch 66) within cassette 42. The switches may be in electrical communication with the heat pad or the solenoid.

Figure 9:
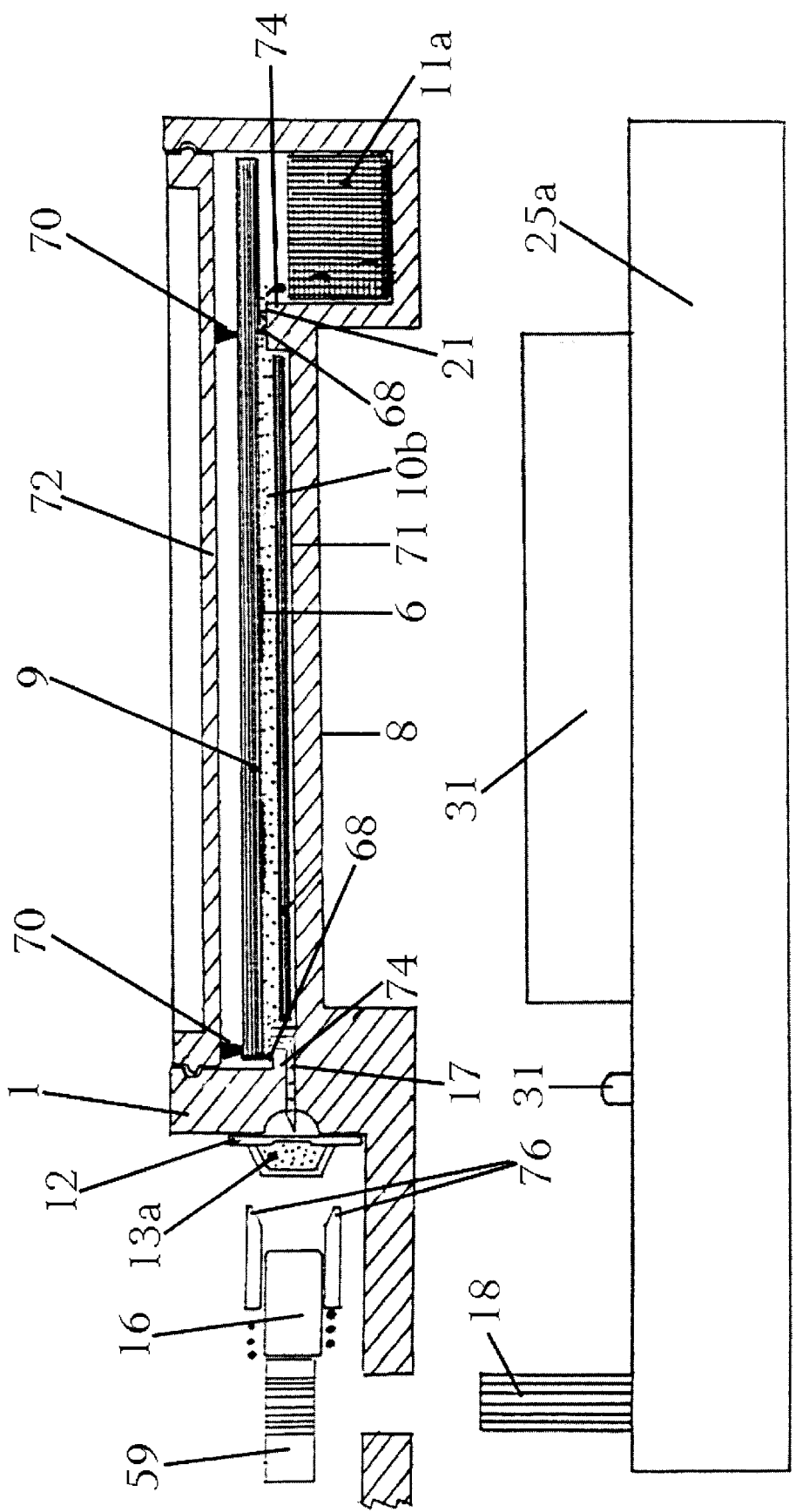
FIG. 9 is a cross-sectional view of a portion of a tissue staining system, including a cassette and a cassette driver.

Turning to FIG. 9, another embodiment of the tissue staining system is presented. Cassette 1 is preferably shaped to receive different elements of the staining system. Cassette 1 preferably includes a cavity 71 and a removable cap 72 which acts as a closure device for cavity 71. Cap 72 is preferably shaped to snap into a wall surrounding a top portion of cavity 71. When cap 72 is removed, plate 8 may be positioned across the bottom of cavity 71. Cassette 1 may further include a raised protrusion 74 on sides of cavity 71. Specimen slide 9 may be placed a predetermined distance above plate 8 such that a sealing element 68 (i.e., a spacer) is located between the edges of specimen slide 9 and each protrusion 74 to form a head space 10b between plate 8 and specimen slide 9. Thus, unlike previously depicted embodiments, specimen slide 9 is not connected to plate 8 while tissue sample 6 is being stained. The side of specimen slide 9 which contains tissue sample 6 preferably faces head space 10b. Therefore, tissue sample 6 may protrude downward from slide 9. Another sealing element 70 may be placed above the outer edges of slide 9, and cap 72 may be snapped into cassette 1 such that it abuts sealing element 70. Cap 72 preferably locks specimen slide 9 and plate 8 within cavity 71. Injection port 17 and relief port 68 are preferably formed within cassette 1 and communicate with head space 10b. Injection port 17 and relief port 68 are preferably located at opposite ends of head space 10b to allow a chemical to pass into and out of head space 10b. A waste tank 11a may be disposed within cassette 1 underneath relief port 21 to collect any chemical exiting from head space 10b.

Film 12 preferably carries a chemically filled container 13a to a position adjacent to injection port 17. Piston 16 is preferably aligned with injection port 17. When cassette 1 is placed onto cassette driver 25a, cassette driver 25a may automatically start running because starting switch 31 is triggered by the pressure of cassette 1. Splined shaft 18 preferably extends up from cassette driver 25a and into cassette 1 where it rotates to cause cam 59 to displace piston 16. Piston 16 may push container 13a against a sharp end of injection port 17. Members 76 may help guide piston 16 so that it remains aligned with container 13a. The pointed end of injection port 17 may puncture the wall of container 13a, forming an opening in the wall. The chemical within container 13a may then flow freely into injection port 17 through this opening. Heat pad 20 of cassette driver 25a may be used to heat chemicals passing through head space 10b since it may be positioned under plate 8. After film 12 has delivered all chemicals necessary for the staining procedure, a mounting medium may be injected into head space 10b to form a glue-like substance between specimen slide 9 and plate 8. The "mounting medium" is taken to mean any translucent substance capable of adhering to slide 9 and to plate 8. Thus, specimen slide 9 and plate 8 are permanently connected to form a unit which can be removed from cassette 1 and placed under a microscope for inspection.

Figure 10:
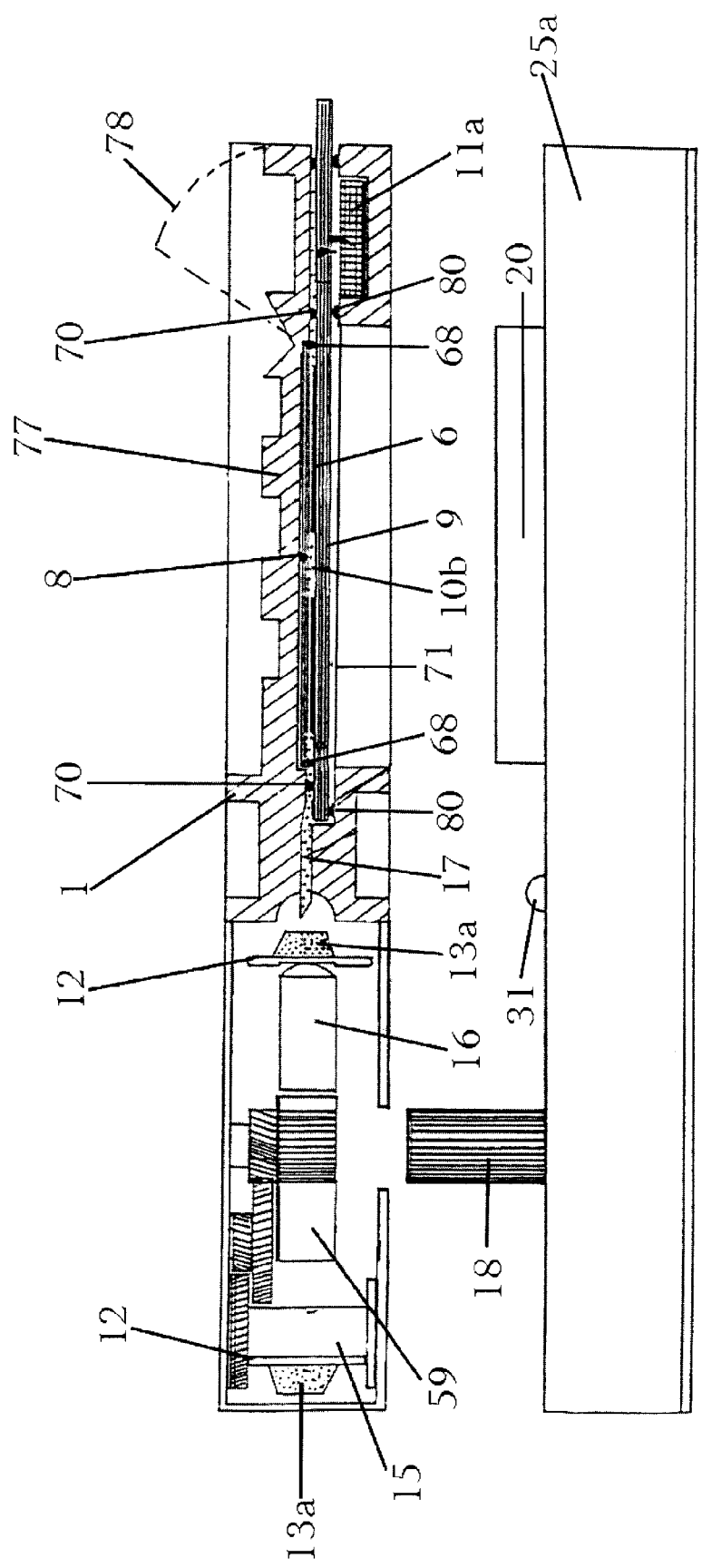
FIG. 10 is a cross-sectional view of a tissue staining system, including a cassette and a cassette driver.

FIG. 10 depicts another embodiment of a tissue staining system which is similar to the embodiment of FIG. 9, with a few exceptions. For example, an upper portion 77 of cassette 1 may be folded back, allowing access to a cavity 71 within cassette 1. One end of upper portion 77 may be lifted upward (shown by dashed line 78) while the opposite end remains attached to cassette 1 so that it works like a door. The end of upper portion 77 attached to cassette 1 may be flexible to enable the lifting mechanism. Upon opening upper portion 77, a sealing element 80 followed by specimen slide 9 may be placed across the bottom of cassette 1. Slide 9 is preferably oriented so that the side containing tissue sample 6 faces upward. Cover plate 9 may be placed a predetermined distance above plate 9 such that sealing element 68 is located underneath the edges of plate 9, forming head space 10b between slide 9 and cover plate 8. Sealing element 70 is then preferably placed on top of portions of slide 9. Upper portion 77 may be seated upon sealing element 70 and cover plate 8 when it is closed. The operation of this system is basically the same as that of the system depicted in FIG. 9.

Figure 11:
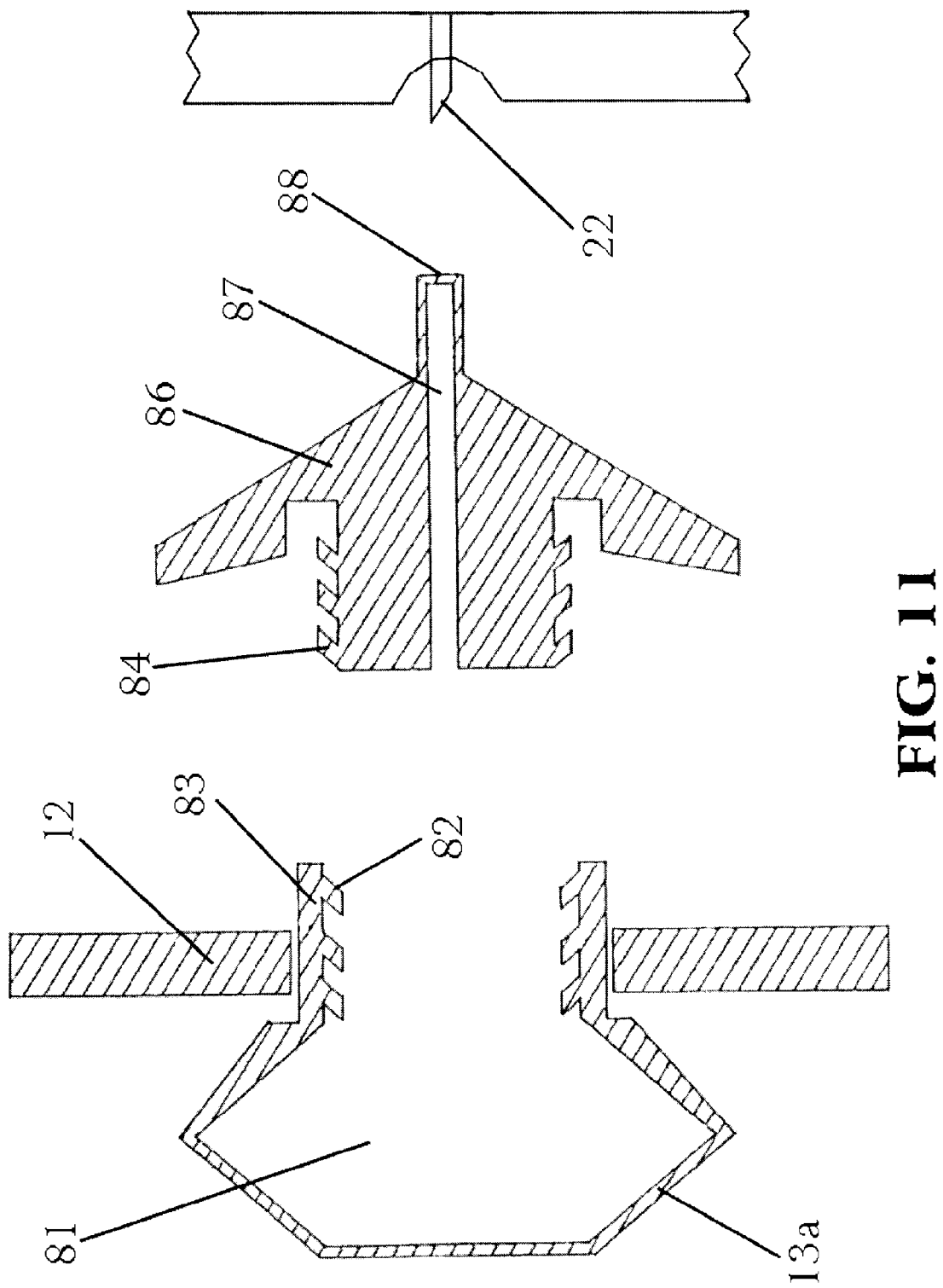
FIG. 11 is a cross-sectional view of the locking mechanism of a chemical container which belongs to a tissue staining system.

Turning to FIG. 11, an embodiment of a chemical container 13a is depicted. Chemical container 13a is preferably connected to film 12 and includes a cavity 81. Hereafter, "cavity" is taken to mean a space and a wall partially enclosing the space. Container 13a may have protrusions 82 spaced along an inner surface of a wall 83 surrounding a portion of cavity 81. Container 13a may be filled with a chemical and then sealed to prevent the chemical from escaping. A container cap 86 may be used to seal container 13a. A portion of cap 86 may be disposed within cavity 81 to plug container 13a. A second set of complementary protrusions 84 preferably line a portion of the outer surface of cap 86. Protrusions 84 are preferably shaped to fit between protrusions 82 so that cap 86 may be locked to the inner surface of wall 83. A slit 87 preferably extends through the center of cap 86 and preferably terminates at another wall 88. When cap 86 is positioned within cavity 81, a chemical within container 13a may enter slit 87. However, wall 88 preferably prevents the chemical from exiting from slit 87. During injection of a chemical into cassette 1, wall 88 may be forced against a pointed end of conduit 22, causing wall 88 to be punctured and releasing a chemical into conduit 22.

Figure 12A:
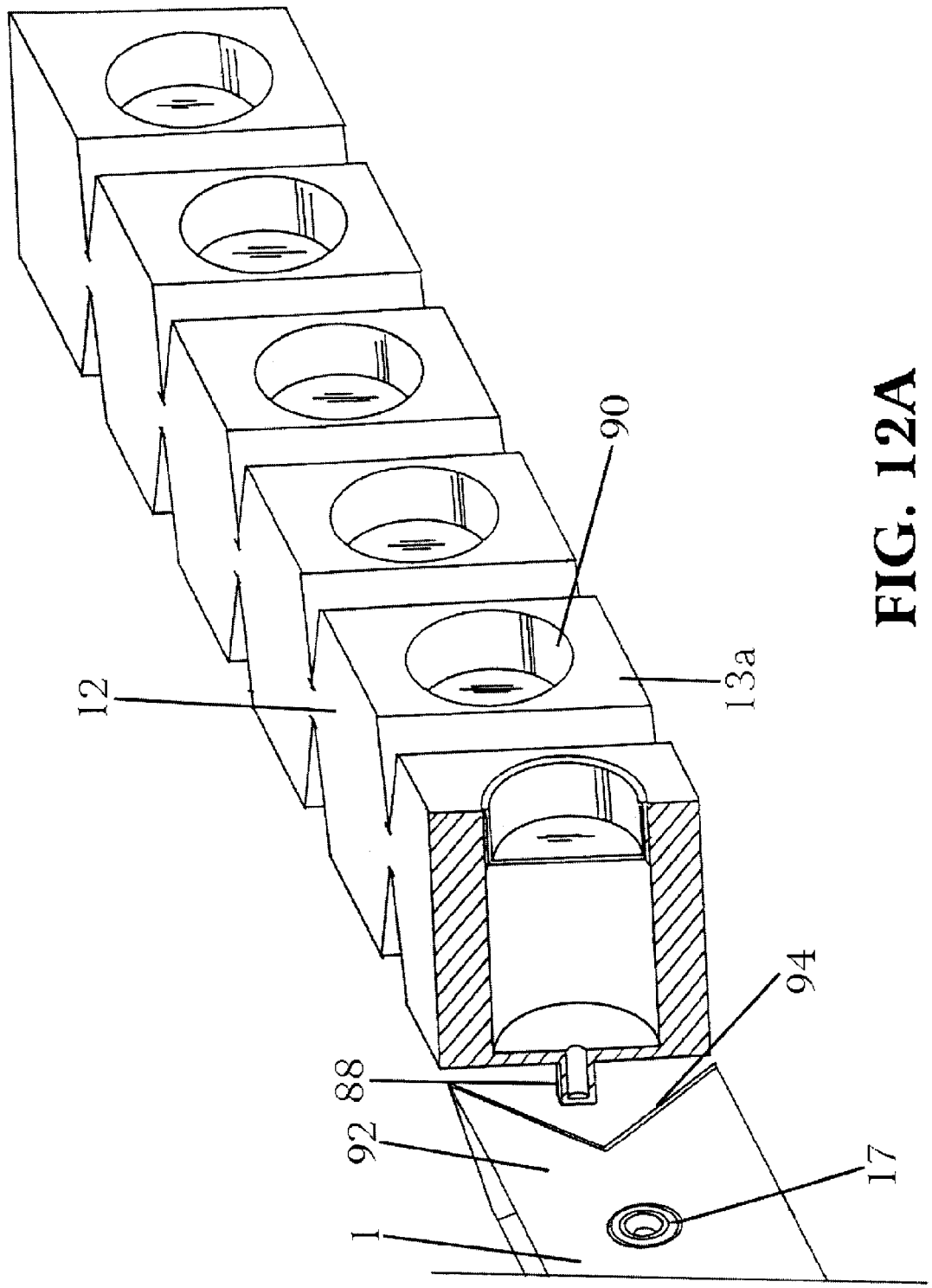
FIG. 12a is a perspective view of a portion of a cassette and a portion of a film belonging to a tissue staining system.
Figure 12B:
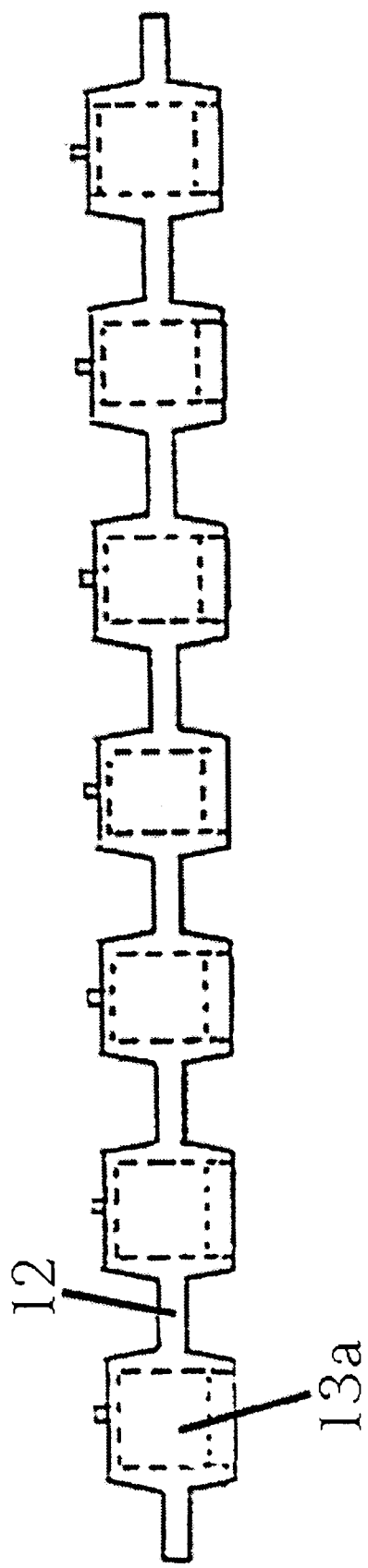
FIG. 12b is a cross-sectional view of a portion of a film belonging to a tissue staining system.

Turning to FIG. 12a, a portion of cassette 1 and a portion of film 12 are illustrated in an embodiment. Cassette 1 may have a substantially V-shaped edge 94. This edge is preferably sharp enough to cut through wall 88 which protrudes from a side of each container 13a. In one embodiment, film 12 carries containers 13a sequentially to injection port 17. As wall 88 of each container 13a comes into contact with edge 94, wall 88 may be removed from container 13a via edge 94 cutting through it. Container 13a preferably abuts surface 92 of cassette 1 to prevent chemicals within container 13a from escaping through the opening created by the removal of wall 88. Then, as container 13a passes by injection port 17, a chemical may flow from container 13a into injection port 17 via the opening. Further, a cavity 90 of container 13a is preferably located opposite to the opening. A piston may be propelled into cavity 90 to help force the chemical into injection port 17. Cavity 90 preferably includes a flexible wall which does not break open under pressure of the piston. FIG. 12b depicts a cross-sectional view of the top of film 12 having containers 13a.

EXPERIMENT

The slide device depicted in FIG. 3 was used to apply various chemicals to tissue samples. Tissue samples were placed into eight positive displacement slide devices having a specimen slide and a cover plate. Each of the slide devices contained a head space between the specimen slide and the cover plate that had a width ranging from 0.0005 inch to 0.004 inch. Sixteen control tissue samples that were each three micrometers thick were mounted in pairs on the eight specimen slides.

Each of the tissue samples was stained as follows using quality-controlled, standardized immunohistochemistry procedures. The slide device and tissue samples were dried at 58° C. for one hour. Pure xylene having essentially no dissolved contaminates of paraffin was injected under pressure into the slide device three sequential times. The third injection of xylene remained in the head space of the slide device for ten minutes before a 100% alcohol composition was injected into the head space. The injection of the alcohol through the injection port forced the excess xylene out of the head space. Three minutes later, peroxide/methanol was injected into the head space to prevent blood and other portions of the tissue from interacting with chemicals which would subsequently be injected. The peroxide remained in the head space for thirty minutes.

The tissue was then rehydrated via injection of a 95% alcohol solution into the head space. After three minutes a deionized water rinse was injected into the head space. Then tissue revival was performed by heating the slide device and sequentially injecting an immunohistochemistry (IHC) rinse into the head space three times. Immediately after injecting the third rinse, a primary antibody for staining the tissue was injected into the head space. The primary antibody remained in the head space for fifteen minutes. An injection of an IHC wash buffer was then performed and immediately followed by an injection of a secondary antibody known as link into the head space. After the link had been in the head space for ten minutes, an IHC wash buffer was injected again. Immediately thereafter, a chemical known as label was injected into the head space where it remained for ten minutes.

Next, an IHC wash buffer was injected into the slide device. Immediately thereafter, a chromogen was injected into the head space to colorize the stains. An optimum 4:1 ratio of desired stained tissue parts to undesired background stained parts was reached after a time period that ranged from approximately thirty seconds to five minutes among the tissue samples, and then a deionized water rinse was injected into the head space. The ratio of desired stained tissue parts to background stained parts was determined using a standardized scoring system well known to those skilled in the art in which 4 is the highest intensity of staining and 1 is the lowest intensity of background. A counterstain was injected to produce color contrast. The counterstain remained in the head space for forty-five seconds and then a deionized water rinse was injected into the head space. Finally, a translucent mounting medium was injected into the head space which acted as a "glue" to seal the cover plate to the head space permanently. The specimen slide and cover plate could then be placed under a microscope as a unit.

The above experiment required only small, efficient amounts of a chemical for staining tissue. Due to varied head space distances the required injected volumes varied from 50 microliters to 200 microliters. The deionized water rinses were quick and completely cleaned the head spaces because previous chemicals were positively displaced from the slide devices. Further, uniform and complete staining was achieved on all sixteen tissue samples.

The above-mentioned results suggest that positive-displacement injection of chemicals such as antibodies and buffers is a viable method for the procedures of immunohistochemisty. The positive displacement of a previously injected chemical from a slide device was found to prevent dilution or mixing between an injected chemical and the previously injected chemical. Chemical waste is reduced as compared to conventional methods, and the flow of chemicals under pressure over tissue tends to cause the tissue to be stained evenly and completely.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. For example, integrated circuit devices which embody central processing units and pre-programmed and/or re-programmable memory may be utilized in the cassette and/or drive unit to control the function of motors, piston actuators, heating pads, and status displays. Such electronic control methodologies could supplement or replace mechanical methodologies described herein.

What is claimed is:

1. A method for applying a chemical to a tissue sample, comprising:

providing a cassette including an endless strip, the endless strip having a multiplicity of chemical containing capsules thereon, the cassette including means to move said endless strip;

placing the tissue sample on a specimen slide;

placing a cover plate over the specimen slide, wherein a head space exists between the specimen slide and the cover plate;

inserting into the cassette the specimen slide to a point where the head space is adjacent to one of the multiplicity of chemical-containing capsules of the endless strip;

forcing by pressure a first chemical into the head space, thereby allowing the first chemical to contact the tissue sample;

moving the endless strip such that a second chemical containing capsule is adjacent to the head space of the slide; and forcing by pressure a second chemical into the head space, thereby positively displacing at least a portion of the first chemical out of the head space.

2. The method of claim 1, wherein the head space has a width between about 0.0005 of an inch and about 0.004 an inch.

3. The method of claim 1, further comprising locating a spacer between the specimen slide and the cover plate to define a width of the head space.

4. The method of claim 1, wherein the cover plate and the specimen slide are comprised in a slide device that further comprises an injection port communicating with the head space, and wherein the step of forcing the first chemical into the head space comprises contacting the capsule with a piston to puncture the capsule and direct the chemical from the container through the injection port.

5. The method of claim 1, wherein the cover plate and the specimen slide are comprised in a slide device that further comprises an injection port and a relief port, both the injection port and the relief port communicating with the head space, and wherein the step of forcing the second chemical into the head space comprises (a) forcing the second chemical through the injection port into the head space and (b) forcing the portion of the first chemical through the relief port out of the head space.

6. The method of claim 1, further comprising delivering a third chemical into the head space substantially simultaneously with the first chemical, and wherein the step of forcing the first chemical into the head space comprises rupturing a container containing the first chemical and the third chemical, the first chemical and the third chemical being separated by an interior wall disposed within the container.

7. The method as recited in claim 1, further comprising delivering a last chemical into the head space, the last chemical being a substantially transparent mounting medium for sealing the specimen slide to the cover plate.

8. The method of claim 1, further comprising passing the first chemical from the head space to a waste tank containing absorbent material.

9. The method of claim 1, further comprising altering the temperature of the tissue sample to control a rate of reaction between the tissue sample and the chemical.

* * * * *